(12) United States Patent
Partain et al.

(10) Patent No.: US 8,935,099 B2
(45) Date of Patent: Jan. 13, 2015

(54) METHOD AND SYSTEM FOR IDENTIFYING, ASSESSING, AND MANAGING CANCER GROWTH RATES AND POTENTIAL METASTASIS

(71) Applicant: Varian Medical Systems, Inc., Palo Alto, CA (US)

(72) Inventors: Larry Partain, Los Altos, CA (US); Mingshan Sun, Menlo Park, CA (US); Edward J. Seppi, Portola Valley, CA (US); Raisa Pavlyuchkova, Mountain View, CA (US); Arundhuti Ganguly, San Jose, CA (US); Stavros Prionas, Menlo Park, CA (US); James E. Clayton, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 13/623,098

(22) Filed: Sep. 19, 2012

(65) Prior Publication Data
US 2013/0071333 A1    Mar. 21, 2013

Related U.S. Application Data

(60) Provisional application No. 61/536,235, filed on Sep. 19, 2011.

(51) Int. Cl.
| | | |
|---|---|---|
| *G01N 33/00* | (2006.01) | |
| *G06F 19/00* | (2011.01) | |
| *G06K 9/62* | (2006.01) | |
| *G01N 33/50* | (2006.01) | |

(52) U.S. Cl.
CPC .......... *G06F 19/3431* (2013.01); *G06K 9/6277* (2013.01); *G06K 2209/053* (2013.01)
USPC ............................................. 702/22; 702/19

(58) Field of Classification Search
CPC ........... C12Q 1/6886; C12Q 2600/106; C12Q 2600/122; C12Q 2600/158
See application file for complete search history.

(56) References Cited

U.S. PATENT DOCUMENTS 5,840,507 A * 11/1998 Fruehauf ...................... 435/7.23
7,394,889 B2    7/2008 Partain et al.
7,660,384 B2    2/2010 Partain et al.

OTHER PUBLICATIONS

Walt Disney Dolphin, "American Society for Clinical Pharmacology and Therapeutics", Clinical Pharmacology and Therapeutics, Feb. 2001, pp. 88-89, vol. 69, No. 2.
Stephen J. Swensen et al., "Pulmonary Nodules: CT Evaluation of Enhancement with Iodinated Contrast Material", Thoracic Radiology, Feb. 1995, pp. 393-398, vol. 194.
Thomas A. Lasko et al., "The Use of Receiver Operating Characteristic curves in Biomedical Informatics", Journal of Biomedical Informatics, 2005, pp. 404-415, vol. 38.
Judah Folkman, "Fighting Cancer by Attacking Its Blood Supply", Scientific American, Sep. 1996, pp. 150-154.
Nicolas D. Prionas et al., "Contrast-enhanced Dedicated Breast CT: Initial Clinical Experience", Radiology, Sep. 2010, pp. 714-723, vol. 256, No. 3.
Stephen J. Swensen et al., "Lung Nodule Enhancement at CT: Prospective Findings" Thoracic Radiology, 1996, pp. 447-455, vol. 201.
Etta D. Pisano et al., "Diagnostic Performance of Digital Versus Film Mammography for Breast-Cancer Screening", The New England Journal of Medicine, Oct. 27, 2005, pp. 1773-1783, vol. 353, No. 17.
A.S. Gokhale et al., Clinical and Dosimetric Factors Associated with a Prolonged Feeding Tube Requirement in Patients Treated with Chemoradiotherapy (CRT) for head and neck cancers, Annals of Oncology, Jul. 14, 2009, pp. 1-7. <doi:10.1093/annonc/mdp268>.
The National Lung Screening Trial Research Team, "Reduced Lung-Cancer Mortality with Low-Dose Computed Tomographic Screening", The New England Journal of Medicine, Aug. 4, 2011, pp. 395-409, vol. 365, No. 5.
Noel Weidner et al., "Tumor Angiogenesis Correlates with Metastasis in Invasive Prostate Carcinoma", American Journal of Pathology, Aug. 1993, pp. 401-409, vol. 143, No. 2.
Elizabeth A Morris, "Should We Dispense With Preoperative Breast MRI?", The Lancet, Feb. 13, 2010, pp. 528-530, vol. 375.
Ahmedin Jemal et al., "Cancer Statistics", CA Cancer J Clin, 2010, pp. 277-300, vol. 60.
Peng Wang et al., "An Approach to Identify, from DCE MRI, Significant Subvolumes of Tumors Related to Outcomes in Advanced Head-and-neck Cancer", Med. Phys., Aug. 2012, pp. 5277-5285, vol. 39, No. 8.
M. Nielsen et al., "Breast Cancer and Atypia Among Young and Middle-aged Women: A Study of 110 Medicolegal Autopsies", Br J. Cancer, 1987, pp. 814-819, vol. 56, The Macmillan Press Ltd.

* cited by examiner

*Primary Examiner* — Eric S Dejong
(74) *Attorney, Agent, or Firm* — SU IP Consulting

(57) ABSTRACT

Techniques described herein generally relate to identifying, assessing, and managing cancer growth rates and potential metastasis. Some example methods may include constructing one or more quantitative metrics for the potential metastasis in a selected population of other patients, acquiring a first set of numeric biomarker data for the patient before having placed a biomarker in the patient, acquiring a second set of numeric biomarker data for the patient after having placed the biomarker in the patient, determining a set of biomarker surrogate values for microvessel density information based on a mean numeric biomarker difference derived from the first set of numeric biomarker data and the second set of numeric biomarker data, determining a set of biomarker surrogate values for microvessel density information based on a mean numeric biomarker difference derived from the first set of numeric biomarker data and the second set of numeric biomarker data, and predicting quantitative and objective risk for the cancer growth rates and potential metastasis and adjusting a treatment plan based on the biomarker surrogate values and at least one of the one or more quantitative metrics.

8 Claims, 25 Drawing Sheets

300

Lung Cancer ROC Data

| ΔAH₁ₜₓ₋σ (w/sv-σ iodine) | $i_c$ (mg/ml) | Number of Nodules Benign | Number of Nodules Malignant | TP | TN | FP | FN |
|---|---|---|---|---|---|---|---|
| -10 | -0.7 | 1.211 | 0.001 | 111.0 | 1.2 | 55.8 | 0.0 |
| -8 | -0.4 | 1.856 | 0.006 | 111.0 | 1.2 | 54.6 | 0.0 |
| -6 | -0.3 | 2.384 | 0.011 | 111.0 | 3.2 | 52.6 | 0.0 |
| -4 | -0.1 | 2.761 | 0.020 | 111.0 | 5.5 | 50.3 | 0.0 |
| -2 | 0.0 | 3.119 | 0.033 | 111.0 | 8.3 | 47.5 | 0.0 |
| 0 | 0.1 | 3.407 | 0.061 | 111.0 | 11.4 | 44.4 | 0.1 |
| 2 | 0.3 | 3.595 | 0.102 | 111.0 | 14.8 | 41.0 | 0.1 |
| 4 | 0.4 | 3.678 | 0.165 | 111.0 | 18.4 | 37.4 | 0.2 |
| 6 | 0.5 | 3.657 | 0.263 | 111.0 | 22.1 | 33.7 | 0.4 |
| 8 | 0.7 | 3.482 | 0.403 | 111.0 | 25.7 | 30.1 | 0.7 |
| 10 | 0.8 | 3.232 | 0.604 | 111.0 | 29.2 | 26.6 | 1.1 |
| 12 | 0.9 | 2.913 | 0.875 | 111.0 | 32.4 | 23.4 | 1.7 |
| 14 | 1.1 | 2.555 | 1.231 | 111.0 | 35.4 | 20.4 | 2.5 |
| 16 | 1.2 | 2.191 | 1.680 | 111.0 | 37.9 | 17.9 | 3.8 |
| 18 | 1.3 | 1.843 | 2.227 | 111.0 | 40.1 | 15.7 | 5.5 |
| 20 | 1.5 | 1.548 | 2.864 | 108.0 | 42.0 | 13.9 | 7.7 |
| 22 | 1.6 | 1.301 | 3.576 | 104.0 | 43.5 | 12.3 | 10.6 |
| 24 | 1.7 | 1.114 | 4.334 | 100.0 | 44.6 | 11.0 | 14.1 |
| 26 | 1.9 | 0.983 | 5.098 | 96.0 | 45.9 | 9.9 | 18.5 |
| 28 | 2.0 | 0.894 | 5.822 | 94.0 | 46.9 | 8.9 | 23.6 |
| 30 | 2.0 | 0.849 | 6.453 | 86.0 | 47.8 | 8.0 | 29.4 |
| 32 | 2.3 | 0.858 | 6.924 | 75.0 | 48.6 | 7.2 | 35.8 |
| 34 | 2.4 | 0.784 | 7.252 | 72.0 | 49.4 | 6.4 | 42.8 |
| 36 | 2.5 | 0.759 | 7.353 | 65.0 | 50.2 | 5.6 | 50.0 |
| 38 | 2.7 | 0.725 | 7.236 | 55.0 | 51.0 | 4.8 | 57.4 |
| 40 | 2.8 | 0.682 | 6.912 | 48.0 | 51.7 | 4.1 | 64.6 |
| 42 | 2.9 | 0.625 | 6.410 | 42.0 | 52.4 | 3.4 | 71.5 |
| 44 | 3.1 | 0.560 | 5.778 | 35.0 | 53.0 | 2.8 | 77.9 |
| 46 | 3.2 | 0.488 | 5.041 | 31.0 | 53.6 | 2.2 | 83.7 |
| 48 | 3.3 | 0.413 | 4.273 | 25.0 | 54.1 | 1.7 | 88.8 |
| 50 | 3.5 | 0.339 | 3.528 | 23.0 | 54.5 | 1.3 | 93.0 |
| 52 | 3.6 | 0.271 | 2.813 | 20.0 | 54.8 | 1.0 | 96.5 |
| 54 | 3.7 | 0.210 | 2.182 | 18.0 | 55.1 | 0.7 | 99.4 |

| ΔAH₁ₜₓ₋σ (w/sv-σ iodine) | $i_c$ (mg/ml) | Number of Nodules Benign | Number of Nodules Malignant | TP | TN | FP | FN |
|---|---|---|---|---|---|---|---|
| 58 | 3.9 | 0 | 1.643 | 15 | 55.29 | 0.512 | 101.5 |
| 60 | 4.0 | 0 | 1.203 | 12 | 55.45 | 0.354 | 103.2 |
| 62 | 4.1 | 0 | 0.852 | 9 | 55.57 | 0.238 | 104.4 |
| 64 | 4.3 | 0 | 0.587 | 8 | 55.65 | 0.156 | 105.2 |
| 66 | 4.4 | 0 | 0.392 | 5 | 55.71 | 0.100 | 105.9 |
| 68 | 4.5 | 0 | 0.255 | 4 | 55.75 | 0.062 | 106.1 |
| 70 | 4.7 | 0 | 0.160 | 3 | 55.77 | 0.038 | 106.5 |
| 72 | 4.8 | 0 | 0.098 | 3 | 55.79 | 0.022 | 106.6 |
| 74 | 4.9 | 0 | 0.058 | 2 | 55.79 | 0.013 | 106.7 |
| 76 | 5.1 | 0 | 0.034 | 2 | 55.80 | 0.007 | 106.8 |
| 78 | 5.2 | 0 | 0.019 | 1 | 55.80 | 0.004 | 106.8 |
| 80 | 5.3 | 0 | 0.010 | 1 | 55.81 | 0.002 | 106.8 |
| 82 | 5.5 | 0 | 0.005 | 1 | 55.81 | 0.001 | 106.9 |
| 84 | 5.6 | 0 | 0.003 | 1 | 55.81 | 5.12E-04 | 106.9 |
| 86 | 5.7 | 0 | 0.001 | 1 | 55.81 | 2.48E-04 | 106.9 |
| 88 | 5.9 | 0 | 6.56E-04 | 1 | 55.81 | 1.16E-04 | 106.9 |
| 90 | 6.0 | 0 | 3.07E-04 | 1 | 55.81 | 5.32E-05 | 106.9 |
| 92 | 6.1 | 0 | 1.39E-04 | 1 | 55.81 | 2.36E-05 | 106.9 |
| 94 | 6.3 | 0 | 6.15E-05 | 1 | 55.81 | 1.02E-05 | 106.9 |
| 96 | 6.4 | 0 | 2.63E-05 | 1 | 55.81 | 4.27E-06 | 106.9 |
| 98 | 6.5 | 0 | 1.09E-05 | 1 | 55.81 | 1.74E-06 | 106.9 |
| 100 | 6.7 | 0 | 4.49E-06 | 1 | 55.81 | 6.89E-07 | 106.9 |
| 102 | 6.8 | 0 | 1.72E-06 | 1 | 55.81 | 2.65E-07 | 106.9 |
| 104 | 6.9 | 0 | 6.55E-07 | 1 | 55.81 | 9.98E-08 | 106.9 |
| 106 | 7.1 | 0 | 2.41E-07 | 1 | 55.81 | 3.54E-08 | 106.9 |
| 108 | 7.2 | 0 | 8.64E-08 | 1 | 55.81 | 1.27E-08 | 106.9 |
| 110 | 7.3 | 0 | 3.09E-08 | 0 | 55.81 | 4.33E-09 | 106.9 |
| 112 | 7.5 | 0 | 1.01E-08 | 0 | 55.81 | 1.44E-09 | 106.9 |
| 114 | 7.6 | 0 | 3.32E-09 | 0 | 55.81 | 4.61E-10 | 106.9 |
| 116 | 7.7 | 0 | 1.05E-09 | 0 | 55.81 | 1.42E-10 | 106.9 |
| 118 | 7.9 | 0 | 3.25E-10 | 0 | 55.81 | 4.07E-11 | 106.9 |
| 120 | 8.0 | 0 | 9.73E-11 | 0 | 55.81 | 9.37E-12 | 106.9 |

| Breast Cancer ROC Data | | | | | | | |
|---|---|---|---|---|---|---|---|
| $\Delta HU_{TH}$ (w/w-o iodine) | $I_c$ (mg/ml) | Number of Nodules | | TP | TN | FP | FN |
| | | Benign | Malignant | | | | |
| -20 | -1.3 | 0.65 | 0.00 | 27.7 | 0.7 | 25.6 | 0.0 |
| -10 | -0.7 | 2.06 | 0.00 | 27.6 | 2.7 | 25.0 | 0.0 |
| 0 | 0.0 | 4.24 | 0.02 | 27.6 | 7.0 | 22.9 | 0.0 |
| 10 | 0.7 | 5.76 | 0.13 | 27.6 | 12.7 | 18.7 | 0.2 |
| 20 | 1.3 | 5.17 | 0.53 | 27.5 | 17.9 | 12.9 | 0.7 |
| 30 | 2.0 | 3.18 | 1.56 | 27.0 | 21.1 | 7.7 | 2.2 |
| 40 | 2.7 | 1.56 | 3.38 | 25.4 | 22.6 | 4.6 | 5.6 |
| 50 | 3.3 | 0.94 | 5.35 | 22.0 | 23.6 | 3.0 | 11.0 |
| 60 | 4.0 | 0.80 | 6.18 | 16.7 | 24.4 | 2.1 | 17.2 |
| 70 | 4.7 | 0.64 | 5.22 | 10.5 | 25.0 | 1.3 | 22.4 |
| 80 | 5.3 | 0.39 | 3.22 | 5.3 | 25.4 | 0.6 | 25.6 |
| 90 | 6.0 | 0.18 | 1.45 | 2.1 | 25.6 | 0.3 | 27.0 |
| 100 | 6.7 | 0.06 | 0.48 | 0.6 | 25.6 | 0.1 | 27.5 |
| 110 | 7.3 | 0.01 | 0.11 | 0.1 | 25.6 | 0.0 | 27.6 |
| 120 | 8.0 | 0.00 | 0.02 | 0.0 | 25.6 | 0.0 | 27.7 |

FIG. 10

2400 A computer program product 2402 at least one of one or more instructions for constructing one or more quantitative metrics for the potential metastasis in a selected population of other patients;

one or more instructions for acquiring a first set of numeric biomarker data for the patient before having placed a biomarker in the patient;

one or more instructions for acquiring a second set of numeric biomarker data for the patient after having placed the biomarker in the patient ;

one or more instructions for determining a set of biomarker surrogate values for microvessel density information based on a mean numeric biomarker difference derived from the first set of numeric biomarker data and the second set of numeric biomarker data; or One or more instructions for predicting quantitative and objective risk for the cancer growth rates and potential metastasis and adjusting a treatment plan based on the biomarker surrogate values and at least one of the one or more quantitative metrics.

2404 a signal bearing medium 2406 a communication medium 2408 a computer readable medium 2410 a recordable medium

FIG. 24

METHOD AND SYSTEM FOR IDENTIFYING, ASSESSING, AND MANAGING CANCER GROWTH RATES AND POTENTIAL METASTASIS

CROSS-REFERENCE TO RELATED APPLICATIONS

The present application claims the benefit of the U.S. Provisional Application No. 61/536,235, filed on Sep. 19, 2011. This provisional application, including any appendices or attachments thereof, is hereby incorporated by reference in its entirety.

The present application is related to U.S. patent application Ser. No. 13/623,103, entitled "METHOD AND SYSTEM FOR IDENTIFYING, ASSESSING, AND MANAGING CANCER DISEASE," which is incorporated by reference herein in its entirety.

BACKGROUND

Advances in imaging techniques have lead to early detection of tumors but have had small (approximately 15-30%) impact on those malignant tumor types currently responsible for most patient mortality including lung and breast cancer. Existing techniques fail to provide quantitative and objective metrics to predict which suspect detected nodules would be found malignant if biopsied. For example, standard mammography method relies heavily on the subjective, experience, and non-quantitative judgment of highly trained mammographic radiologists. Specifically, the detection and diagnosis is based on a radiologist visually reading and interpreting two projection X-ray radiographs in the cranio-caudal (CC) and medial-lateral-oblique (MLO) orientations taken with breast compression. In addition, although some improvements have been made in existing techniques to detect smaller tumors, such improvements tend to worsen the problem of over-diagnosis, causing more harm than good. For example, by focusing on detecting the smaller tumors, more false positives (e.g., benign nodules) may also be detected, leading to more resources spent (e.g., performing additional testing or surgery) and potentially more penalties introduced (e.g., permanent loss of lung capacity due to the surgery).

Moreover, there is a growing realization that over-diagnosis and overtreatment of cancer diseases may be widespread, and a significant percentage (e.g., approximately 90%) of cancer patients who die of cancer actually die due to metastasis and not due to the lack of local control in treating the primary tumor(s). Existing techniques also fail to effectively and objectively identify, assess, and manage such malignancies that lead to fatality as well as those that do not due to indolent properties like slow, no or negative growth rates. Diagnosis and treatment of the latter contribute to over-diagnosis and overtreatment.

BRIEF DESCRIPTION OF THE DRAWINGS

FIG. 6 illustrates an example quantitative metric constructed also from the smoothed histogram data of FIG. 4 and expressed in an annotated ROC table;

FIG. 10 illustrates an example quantitative metric constructed also from histogram data of FIG. 8 that have been smoothed and expressed in an annotated ROC table;

FIG. 19(*b*) illustrates a relationship between cumulative survival rates and months after initial treatment;

FIG. 24 is a block diagram illustrating a computer program product 2400 for identifying, assessing, and treating potential metastasis for a patient based on a biomarker surrogate of MVDs.

DETAILED DESCRIPTION

The technical details set forth below enable a person skilled in the art to implement at least some embodiments of the present disclosure to identify, assess, and manage cancer diseases. In this disclosure, the term "lesion" and "nodule" are used interchangeably. Also, the term "biomarker" generally refers to a characteristic that is objectively measured and evaluated as a medical indicator of normal biologic processes, pathogenic processes, or responses to a therapeutic intervention. It should be noted a single specific biomarker's medical accuracy, precision and usefulness can be increased when used in conjunction with other biomarkers that characterize complimentary characteristics including other more biological or biochemical biomarkers such as proteins, metabolites, genomics, and others.

Figure 1:
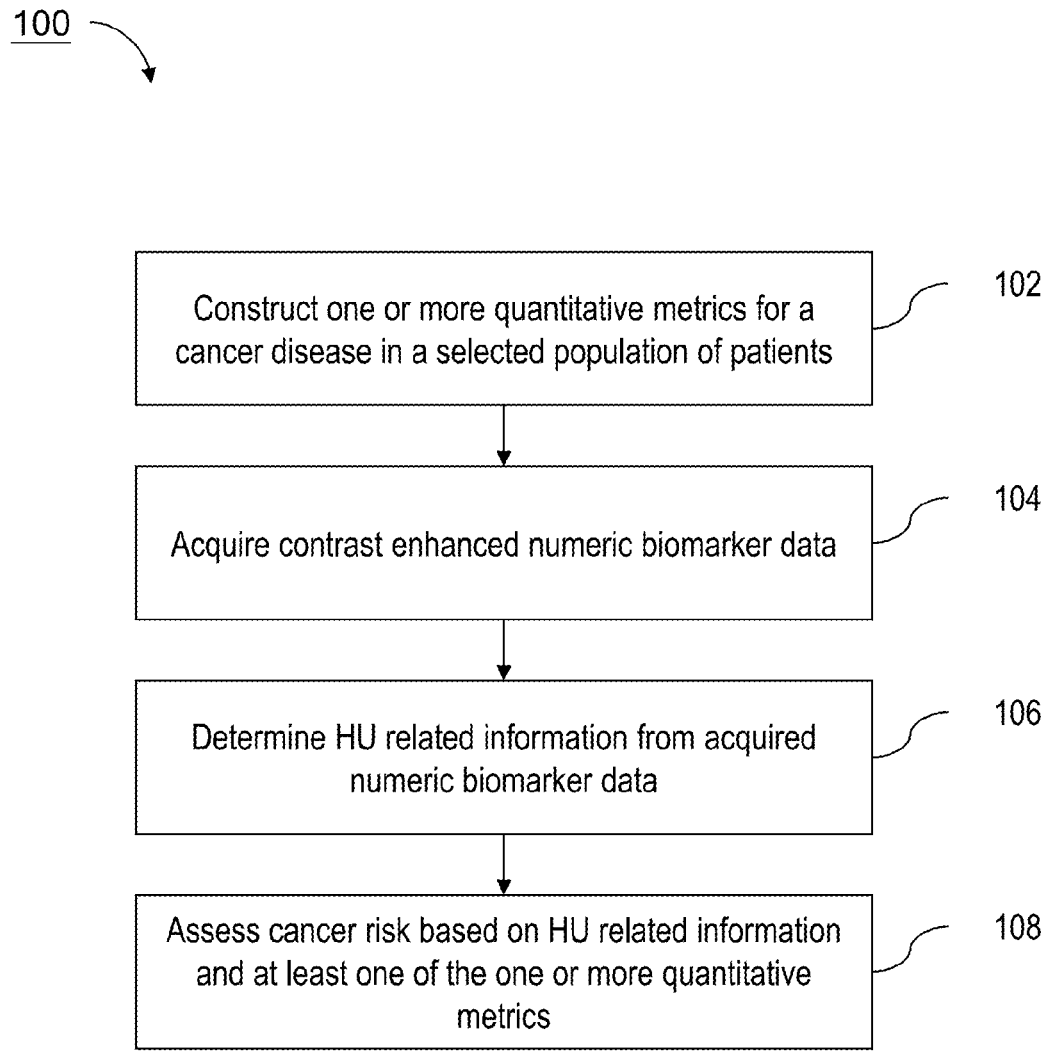
FIG. 1 illustrates an example method 100 of identifying a solid nodule and assessing the risks associated with the identified nodule.

FIG. 1 illustrates an example method 100 of identifying a solid nodule and assessing the risks associated with the identified nodule, in accordance with one embodiment of the present disclosure. The various blocks of the method 100 are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In block 102 (prepare one or more quantitative metrics for a cancer disease in a selected population of patients), relevant data for a selected population of patients for a cancer disease is collected and analyzed, so that one or more quantitative metrics for the selected population of patients may be constructed. Some examples of the relevant data may include, without limitation, numeric biomarker data associated with suspect nodules in the selected population of patients that may be acquired with or without having injected one or more biomarkers into the patients. In addition, the numeric biomarker data may be for various different anatomical sites of the patients, such as, their lungs, breasts, and others. Some example numeric biomarker data may include, without limitation, computed tomography (CT) Hounsfield Unit (HU) values for a contrast agent (e.g., iodine).

With the collected relevant data, some example quantitative metrics, such as, without limitations, sensitivity, specificity, true positive fraction (TPF), false positive fraction (FPF), Receiver Operator Characteristic (ROC) representations, positive predictive value, false negative fraction (FNF), accuracy, prevalence, and others may be constructed. Some of these quantitative metrics correspond to the following equations:

TPF (or sensitivity)=fraction of all malignancies (TP+FN) correctly diagnosed=TP/(TP+FN), where TP corresponds to true positives, and FN corresponds to false negatives;

FPF=fraction of all benign (TN+FP) incorrectly diagnosed=FP/(TN+FP), where TN corresponds to true negatives, and FP corresponds to false positives;

Specificity=fraction of all benign (TN+FP) correctly diagnosed=TN/(TN+FP)

Positive Predictive Value=fraction of positives (TP+FP) that are true=TP/(TP+FP)

FNF=fraction of all negatives (FN+TN) that are actually malignant=FN/(FN+TN)

Accuracy=correct diagnoses (TP+TN) divided by total number of nodules=(TP+TN)/(TN+FN+TP+FP)

Prevalence=fraction of all nodules that were malignant=(TP+FN)/(TN+FN+TP+FP)

Subsequent paragraphs and figures will further detail and illustrate the construction of some of these quantitative metrics.

In block 104 (acquire contrast enhanced numeric biomarker data), according to one embodiment of the present disclosure, a first set of numeric biomarker data associated with a patient being evaluated may be acquired before the injection of the biomarker into the patient (e.g., a contrast agent such as iodine), and a second set of numeric biomarker data may be acquired after the injection of the biomarker into the patient. In an alternative embodiment, one set of numeric biomarker data may be acquired after the injection of the biomarker to reduce or eliminate the X-ray exposure dose. The biomarker's values are physically generated by the concentration gradient of the contrast medium and its physical-chemistry-diffusion through the porous membranes of the angiogenesis capillaries in cancer that changes the physical properties of the region (e.g. linear X-ray attenuation coefficients, mass densities, etc.) that are related to metrics descriptive of solid malignant tumors larger than approximately 1 mm in diameter.

In block 106 (determine HU related information from acquired numeric biomarker data), the acquired numeric biomarker data is further processed to determine HU related information (e.g., a mean HU value, a mean HU enhancement difference value, and others). The different approaches are discussed in subsequent paragraphs.

In block 108 (assess cancer risk based on HU related information and at least one of the one or more quantitative metrics), the HU related information may be utilized (e.g., the difference between the mean HU of an identified nodule with the injected biomarker and the mean HU of the same identified nodule without the injected biomarker) to help quantify cancer risk. Additional details associated with cancer risk assessment are elaborated further in subsequent paragraphs.

Figure 2:
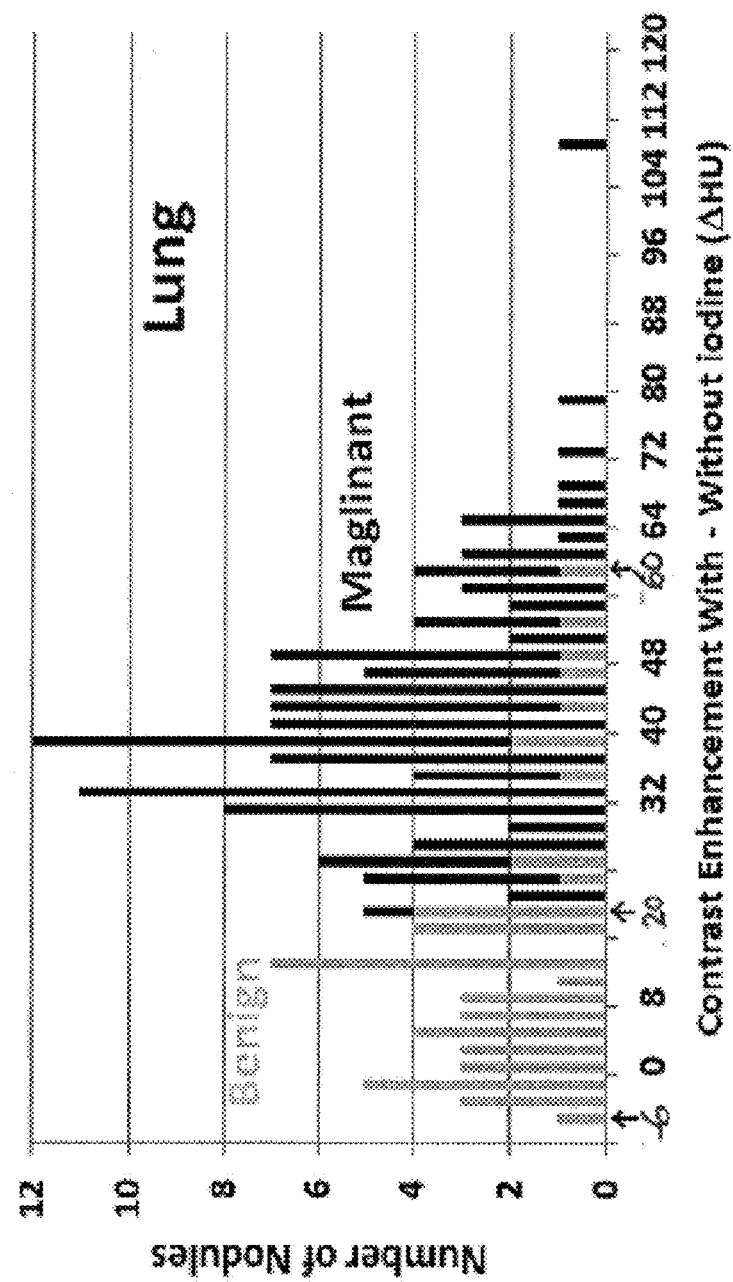
FIG. 2 illustrates an example histogram of a number of solitary pulmonary nodules in the lungs of a selected population of patients that are identified with a set of mean reference Hounsfield Unit (HU) enhancement difference values.

FIG. 2 illustrates an example histogram 200 of a number of solitary pulmonary nodules in the lungs of a selected population of patients that are identified with a set of mean reference HU enhancement difference values ($\Delta HU_{reference}$ value). In one implementation, the vertical axis and the horizontal axis of the histogram 200 correspond to a number of nodules and a set of mean HU enhancement difference values ($\Delta HU$ values), respectively. A biopsy is performed for each of the pulmonary nodules shown in the histogram 200, indicating whether the nodule is considered to be benign or malignant. A benign nodule may be considered as a "false positive," and a malignant nodule may be considered as a "true positive." Also, a first set of CT data without any biomarker (e.g., iodine) enhancement and a second set of CT data with biomarker enhancement are acquired from each of the selected population of patients. For each of the pulmonary nodules shown in the histogram 200, a first mean reference HU value is calculated based on the first set of CT data, and a second mean reference HU value is calculated based on the second set of CT data. Then, the $\Delta HU_{reference}$ value for the pulmonary nodule is obtained by subtracting the first mean reference HU value from the second mean reference HU value.

Figure 3:
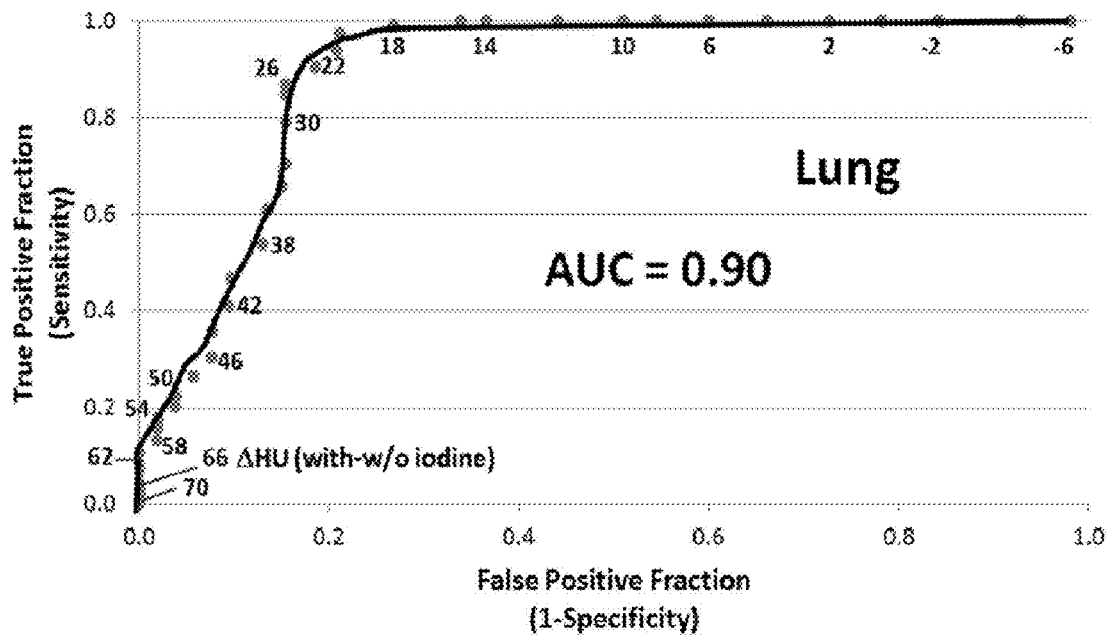
FIG. 3 illustrates an example quantitative metric constructed from the histogram data of FIG. 2 and expressed in an annotated Receiver Operator Characteristic (ROC) curve.

FIG. 3 illustrates an example quantitative metric constructed from the histogram data of FIG. 2 and expressed in an annotated ROC curve 300, in accordance with one embodiment of the present disclosure. The vertical axis of the annotated ROC curve 300 corresponds to TPFs, and the horizontal axis of the annotated ROC curve 300 corresponds to FPFs. TPF and FPF are discussed in earlier paragraphs. In addition, a mean threshold HU enhancement difference value ($\Delta HU_{threshold}$ value) is placed adjacent to some of the data points plotted on the annotated ROC curve 300. Specifically, in one implementation, each $\Delta HU_{threshold}$ value in FIG. 3 corresponds to a certain $\Delta HU_{reference}$ value plotted in FIG. 2, from which certain statistical relationships may be derived. For each of such annotated data points, TP corresponds to a number of true positives at or above the $\Delta HU_{threshold}$ value, and FP corresponds to a number of false positives also at or above the same $\Delta HU_{threshold}$ value.

To illustrate, suppose the $\Delta HU_{threshold}$ value is −6. As shown in FIG. 2, all of the FPs (i.e., benign nodules) and all of the TPs (i.e., malignant nodules) are at or above this −6 value. This corresponds to the TPF=1.0 and FPF=1.0 as shown in FIG. 3. When the $\Delta HU_{reference}$ value goes from −6 to 20 as shown in FIG. 2, the first TP is plotted in the histogram 200. In other words, the annotated ROC curve 300 stays at TPF=1.0 until the corresponding $\Delta HU_{threshold}$ value reaches 20, because the fraction drops. As the $\Delta HU_{threshold}$ value on the annotated ROC curve 300 continues to increase, both the TPF and the FPF monotonically decrease until the $\Delta HU_{threshold}$ value of 60 is reached. Beyond this point, as shown in FIG. 2, there are no more remaining FPs, so the FPF in FIG. 3 then goes to zero.

Figure 4:
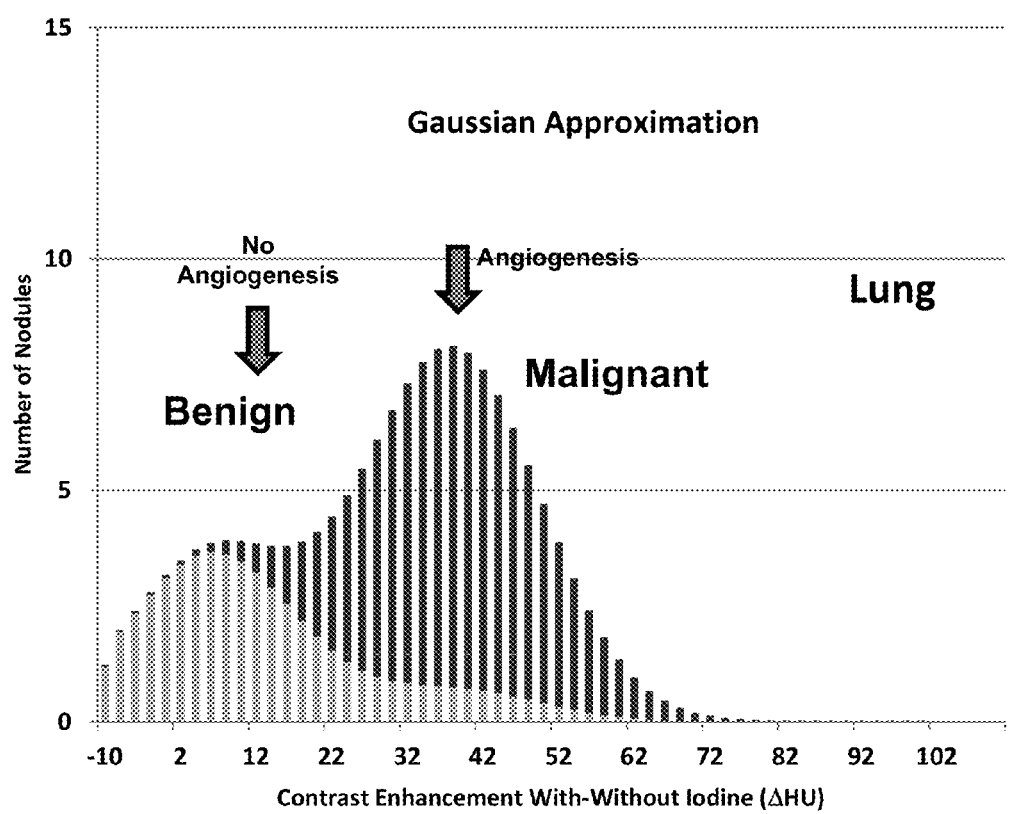
FIG. 4 illustrates an example smoothing of the histogram data of FIG. 2, in accordance with one embodiment of the disclosure.

FIG. 4 illustrates an example smoothing of the histogram data of FIG. 2, in accordance with one embodiment of the present disclosure. Based on the concept that medical diagnosis may be considered a random sampling process described by Normal or Gaussian probability distributions, not only is the shape of the distributions determined by the mean and standard deviation values, but a limited number of samples may also be sufficient to accurately specify means and standard deviations of randomly sampled distributions.

In one implementation, a Gaussian approximation 400 of the histogram data of FIG. 2 includes 3 distributions. Two are the benign distributions, the larger on the left with no angiogensis (i.e., the first benign distribution) and the smaller one on the right with angiogensis (i.e., the second benign distribution). The third and largest distribution where these samples are both angiogenic and malignant. All three of these Normal distributions may be multiplied by the actual number of nodules estimated to come from each distribution. This normalization makes the total number of nodules the same before and after the smoothing. The mean and standard deviation of the first benign distribution may be obtained from the data points up to the $\Delta HU_{reference}$ value of approximately 30, and the mean and standard deviation of the second benign distribution may be obtained from the data points to the $\Delta HU_{reference}$ value of above approximately 30. The latter may assume the same mean and standard deviation as that of the largest and malignant distribution.

Figure 5:
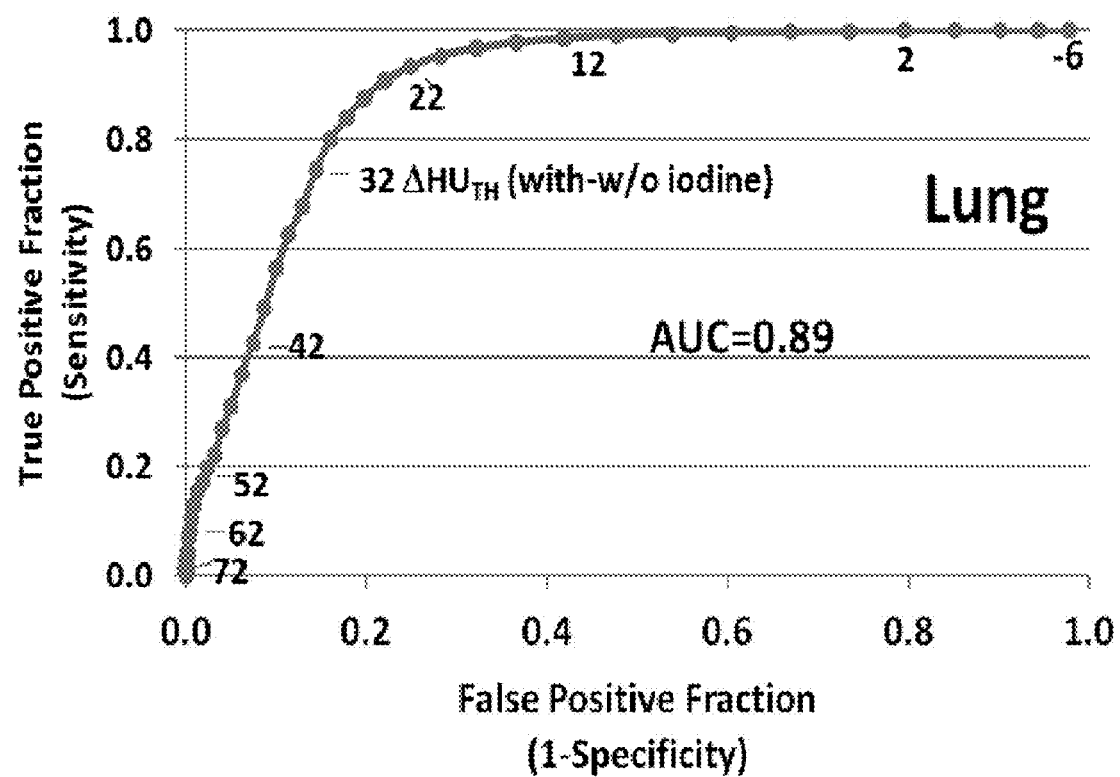
FIG. 5 illustrates an example quantitative metric constructed from the smoothed histogram data of FIG. 4 and expressed in an annotated ROC curve.

FIG. 5 illustrates an example quantitative metric constructed from the smoothed histogram data of FIG. 4 and expressed in an annotated ROC curve 500, in accordance with one embodiment of the present disclosure. With the smoothed histogram data, the accuracy in the characteristics associated with the annotated ROC curve 500 may be improved.

FIG. 6 illustrates an example quantitative metric constructed also from the smoothed histogram data of FIG. 4 and expressed in an annotated ROC table 600, in accordance with one embodiment of the present disclosure.

Figure 7:
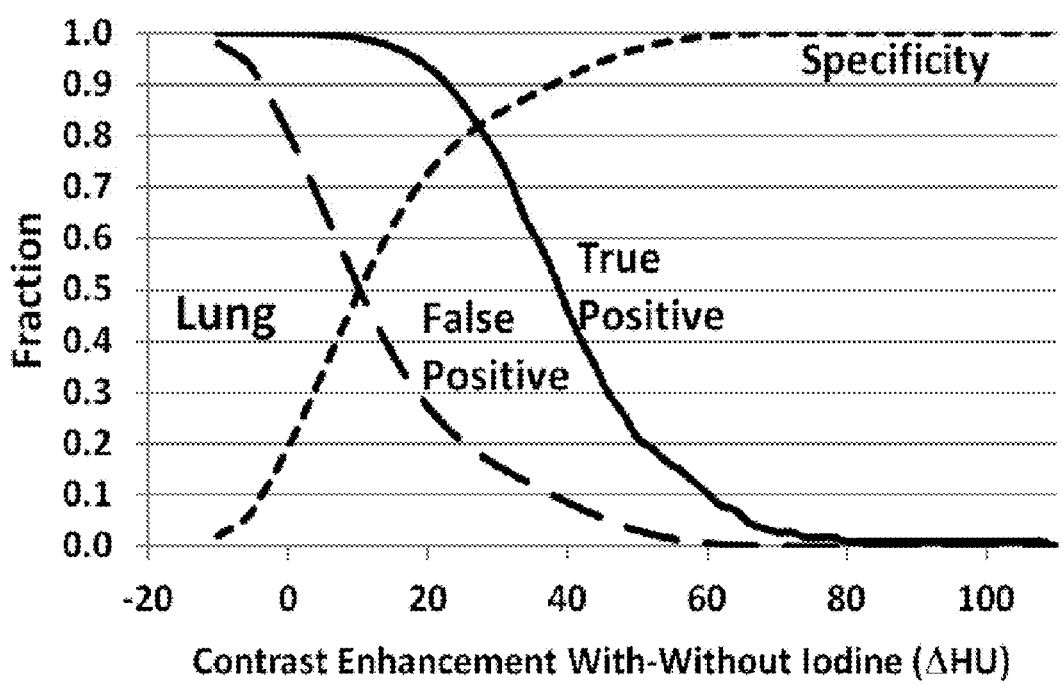
FIG. 7 illustrates an example quantitative metric constructed from the true positive fraction, false positive fraction, and specificity derived from the smoothed histogram of FIG. 4.

FIG. 7 illustrates an example quantitative metric constructed from the true positive fraction, false positive fraction, and specificity derived from the smoothed histogram of FIG. 4, in accordance with one embodiment of the present disclosure. An example graph 700 includes fractions as its vertical axis and a set of $\Delta HU$ values as its horizontal axis. The resulting three curves for the selected population of patients in the graph 700 enable a person, not necessarily a highly trained radiologist, to objectively estimate the false positive, true positive, and specificity values associated with a nodule of a patient being evaluated based on the $\Delta HU$ value for the nodule and also the graph 700.

Figure 8:
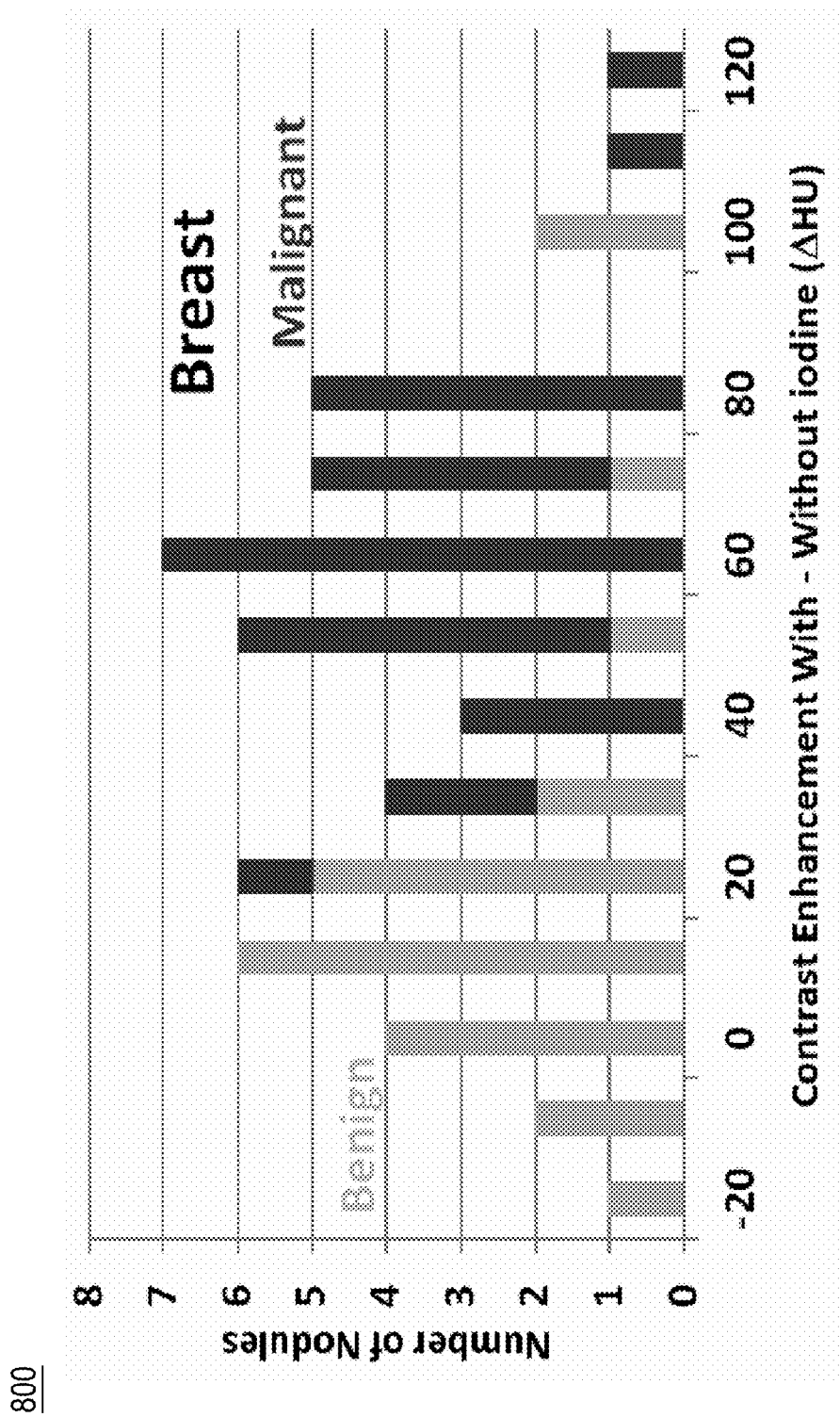
FIG. 8 illustrates an example histogram of a number of nodules in another anatomical site, the breasts, of a selected population of patients that are identified with a set of mean reference HU enhancement difference values.

FIG. 8 illustrates an example histogram 800 of a number of nodules in another anatomical site, the breasts, of a selected population of patients that are identified with a set of $\Delta HU_{reference}$ values.

Figure 9:
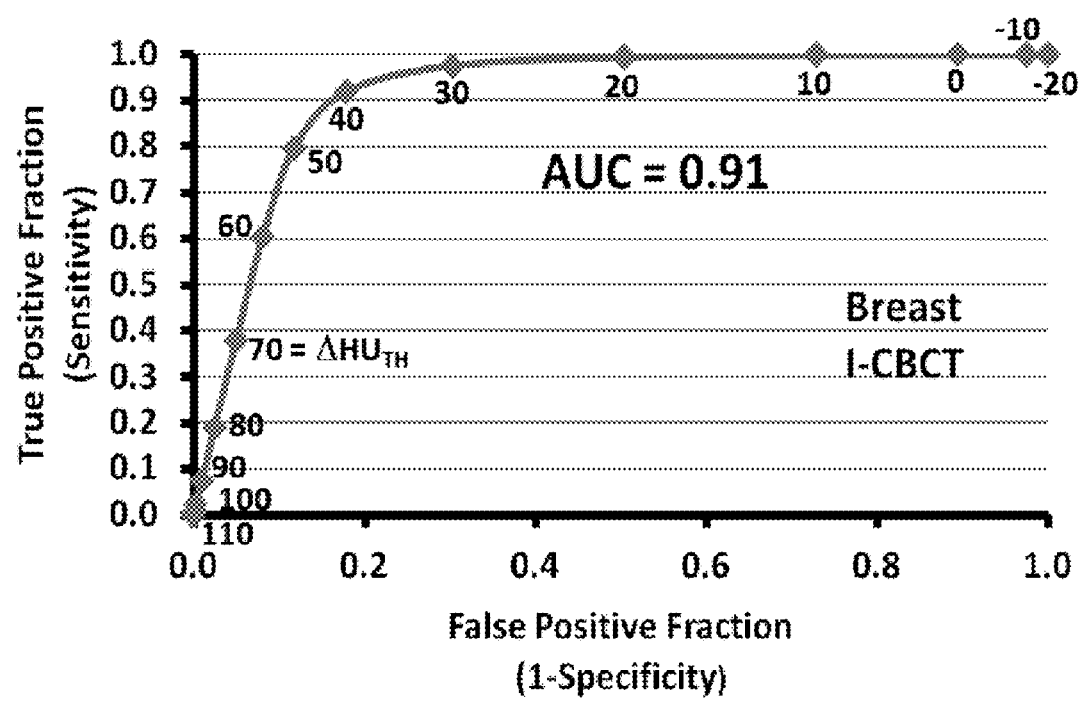
FIG. 9 illustrates an example quantitative metric constructed from the histogram data of FIG. 8 that have been smoothed and expressed in an annotated ROC curve.

Similar to FIG. 5, FIG. 9 illustrates an example quantitative metric constructed from the histogram data of FIG. 8 that have been smoothed and expressed in an annotated ROC curve 900, in accordance with one embodiment of the present disclosure. In one implementation, similar to the smoothing operation shown in FIG. 4 and discussed above, the histogram data of FIG. 8 are Gaussian smoothed.

Similar to FIG. 6, FIG. 10 illustrates an example quantitative metric constructed also from histogram data of FIG. 8 that have been smoothed and expressed in an annotated ROC table 1000, in accordance with one embodiment of the present disclosure.

Figure 11:
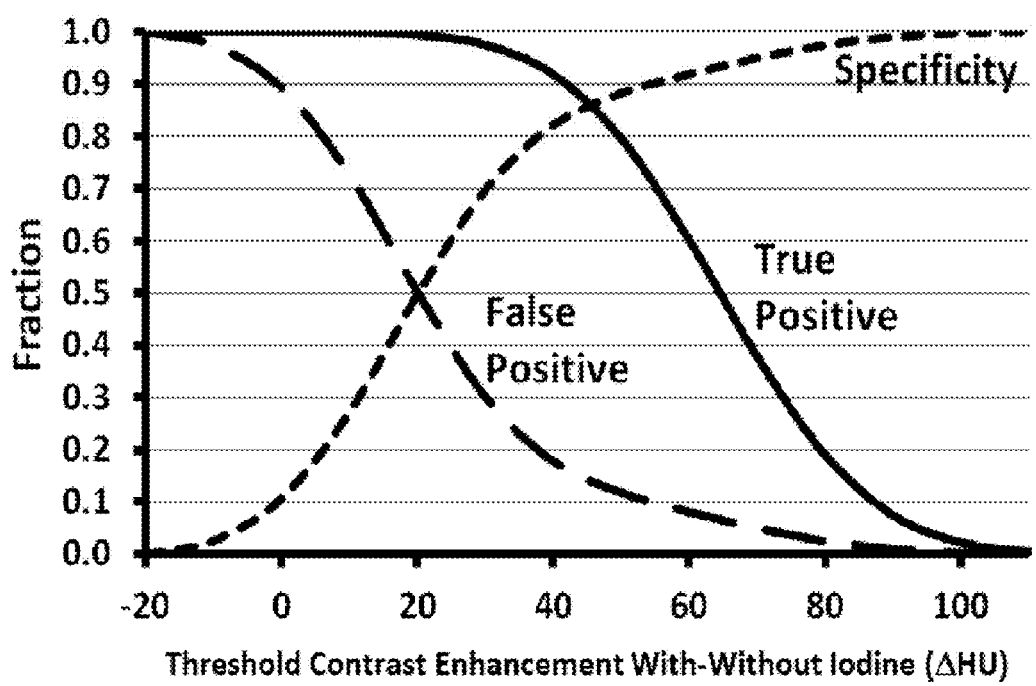
FIG. 11 illustrates an example quantitative metric constructed from the true positive fraction, false positive fraction, and specificity derived from the histogram data of FIG. 8 that have been smoothed.

Similar to FIG. 7, FIG. 11 illustrates an example quantitative metric constructed from the true positive fraction, false positive fraction, and specificity derived from the histogram data of FIG. 8 that have been smoothed, in accordance with one embodiment of the present disclosure.

Figure 12:
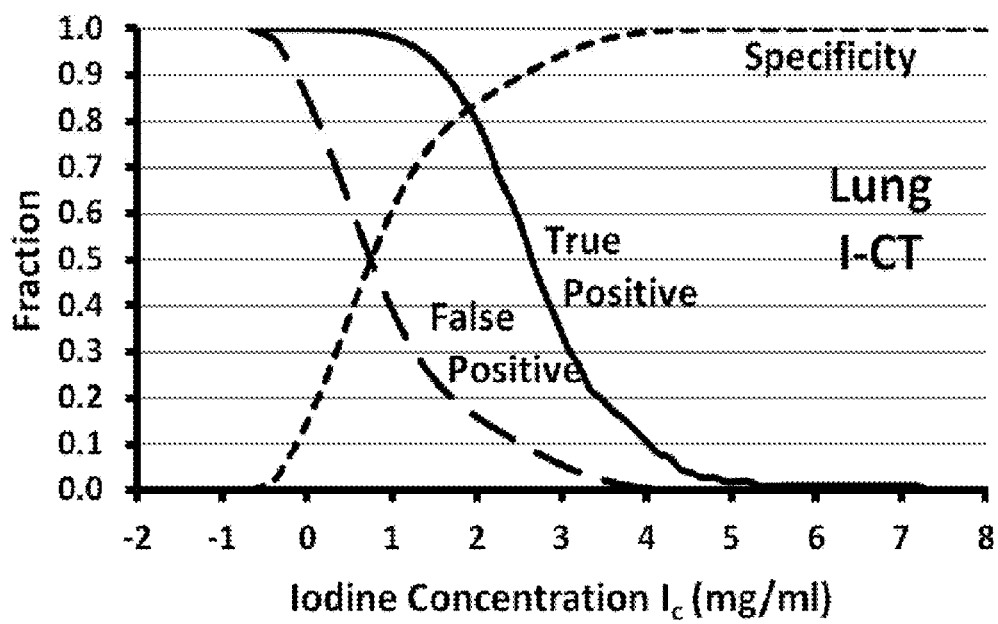
FIG. 12 illustrates an example quantitative metric constructed from the true positive fraction, false positive fraction, and specificity derived from the smoothed histogram of FIG. 4.

FIG. 12 illustrates an example quantitative metric constructed from the true positive fraction, false positive fraction, and specificity derived from the smoothed histogram of FIG. 4, in accordance with one embodiment of the present disclosure. Instead of plotting against a set of $\Delta HU$ values, an example graph 1200 includes fractions as its vertical axis and a set of iodine concentration values ($I_c$) as its horizontal axis. In one implementation, CT HU values have been observed to be linear in iodine concentration with a 600 HU change as the iodine concentration in test samples is raised from 0 to 40 mg/mL. This corresponds to 15 HU change per mg/mL of iodine used as a conversion factor from $\Delta HU$ in Hounsfield Units to iodine concentration $I_c$ in mg/mL.

Figure 13:
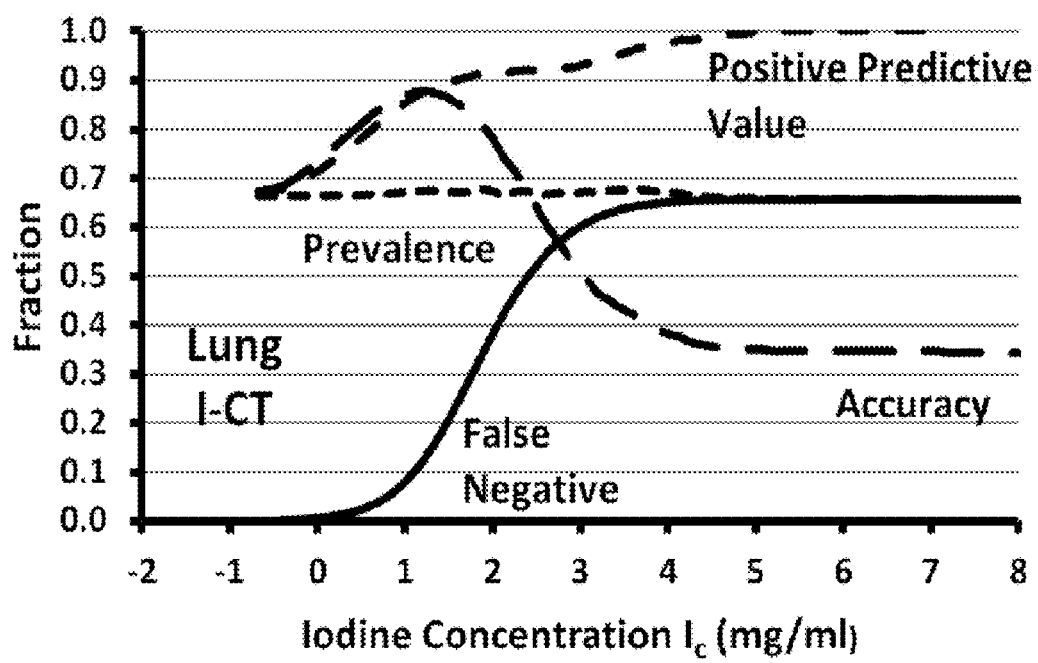
FIG. 13 illustrates an example quantitative metric constructed from the positive predictive value, prevalence, accuracy, and false negative derived from the smoothed histogram of FIG. 4.

FIG. 13 illustrates an example quantitative metric constructed from the positive predictive value, prevalence, accuracy, and false negative derived from the smoothed histogram of FIG. 4, in accordance with one embodiment of the present disclosure. Similar to FIG. 12, an example graph 1300 also includes fractions as its vertical axis and $I_c$ as its horizontal axis.

Figure 14:
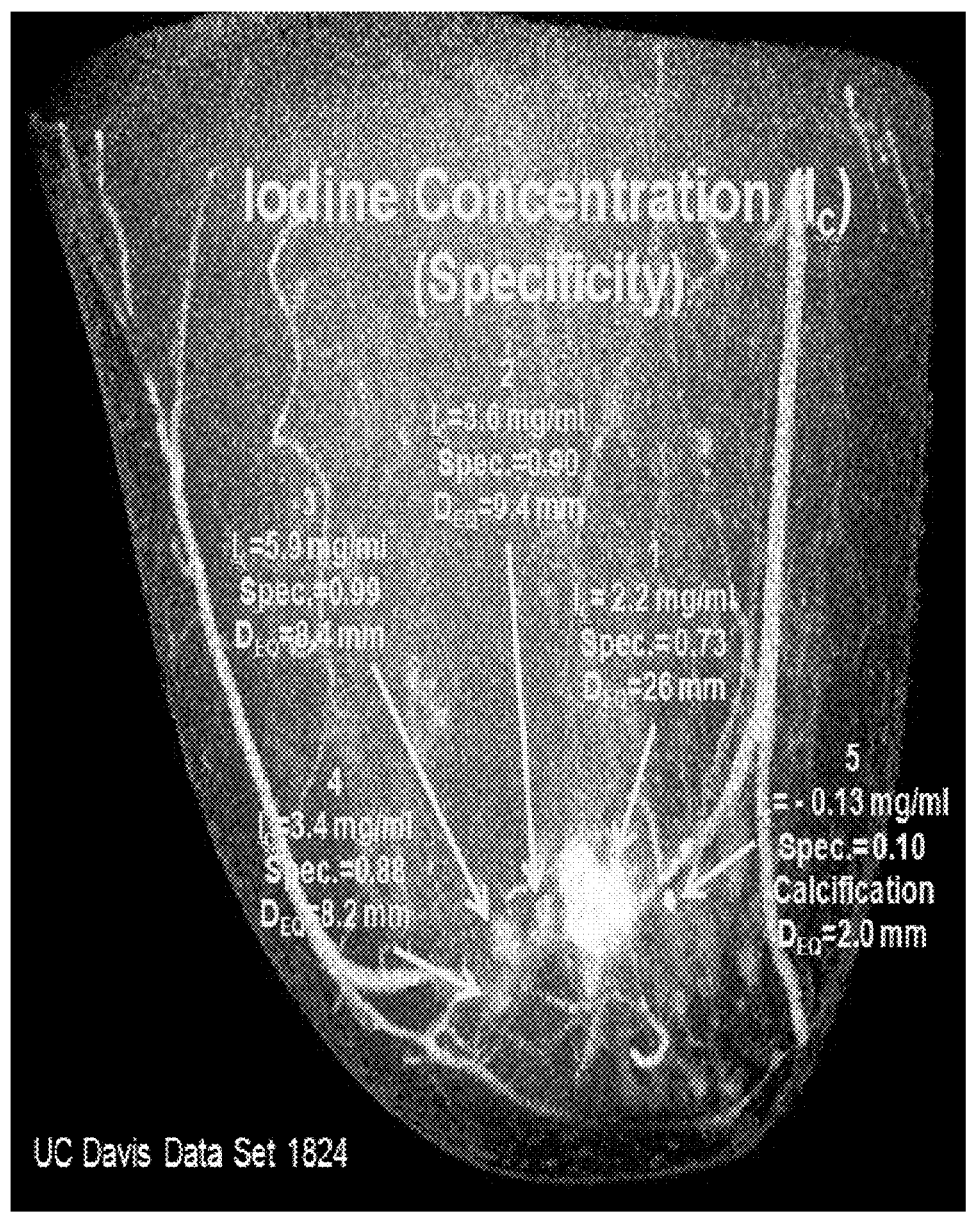
FIG. 14 illustrates an example Maximum Intensity Projection (MIP) image from a breast cancer patient.

FIG. 14 illustrates an example Maximum Intensity Projection (MIP) image 1400 from a breast cancer patient, where the largest nodule shown as Number 1 is biopsy confirmed to be malignant. The ΔHU value for each of the five nodules identified in the MIP image 1400 of a patient being evaluated may be converted to $I_C$ values by dividing the ΔHU value by the 15 HU per iodine mg/ml conversion factor. In addition, for the values shown in FIG. 14, the higher the specificity associated with a lesion, the higher the probability that biopsy determination would show this lesion to be malignant.

Figure 15:
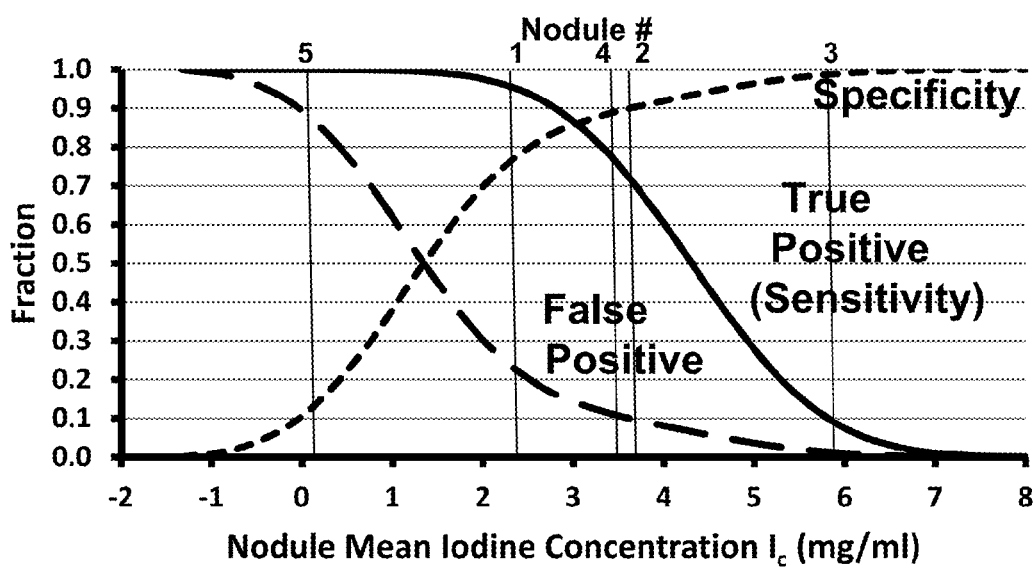
FIG. 15 illustrates an example quantitative metric, such as the graph of FIG. 12, being used to assess multiple nodules identified in a patient being evaluated.

FIG. 15 illustrates an example quantitative metric, such as the graph 1200 of FIG. 12, being used to assess multiple nodules identified in a patient being evaluated, in accordance with one embodiment of the disclosure. To illustrate, the five nodules identified in the MIP image 1400 are plotted in a graph 1500, and the intersections with any of the three curves (i.e., specificity, TPF, and FPF) correspond to numeric metric values.

Figure 16:
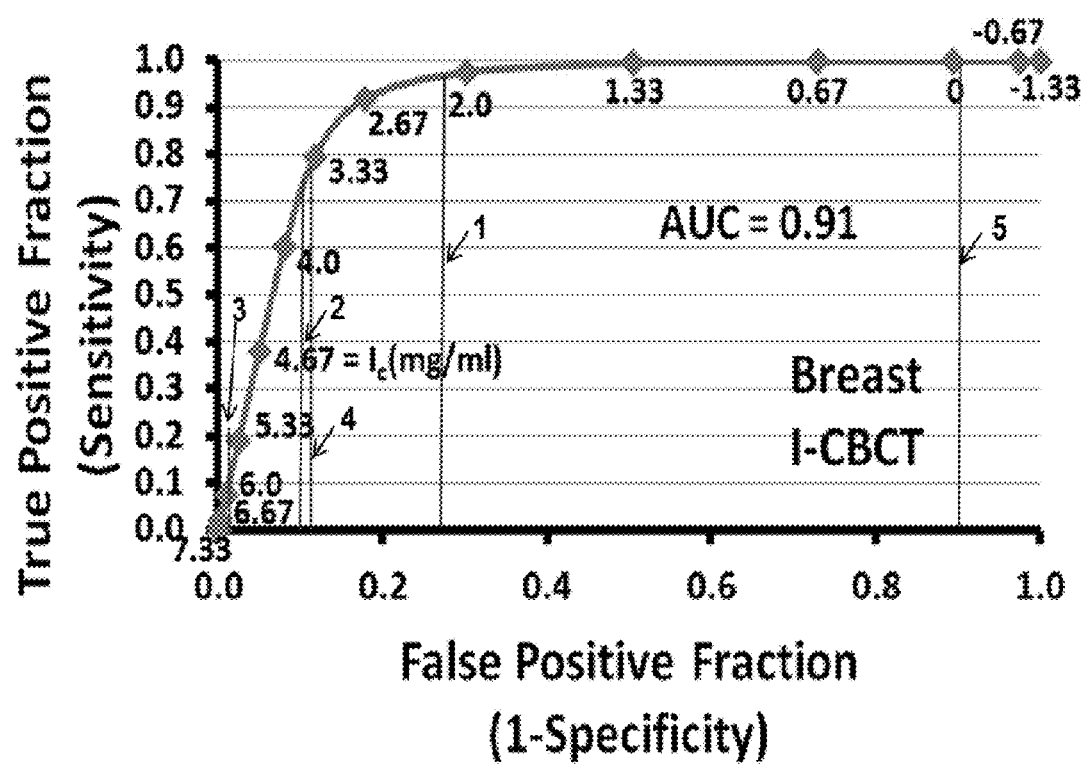
FIG. 16 illustrates another example quantitative metric, such as the annotated ROC curve of FIG. 9, being used to assess multiple nodules identified in a patient being evaluated.

FIG. 16 illustrates another example quantitative metric, such as the annotated ROC curve 900 of FIG. 9, being used to assess multiple nodules identified in a patient being evaluated, in accordance with one embodiment of the disclosure.

Figure 17:
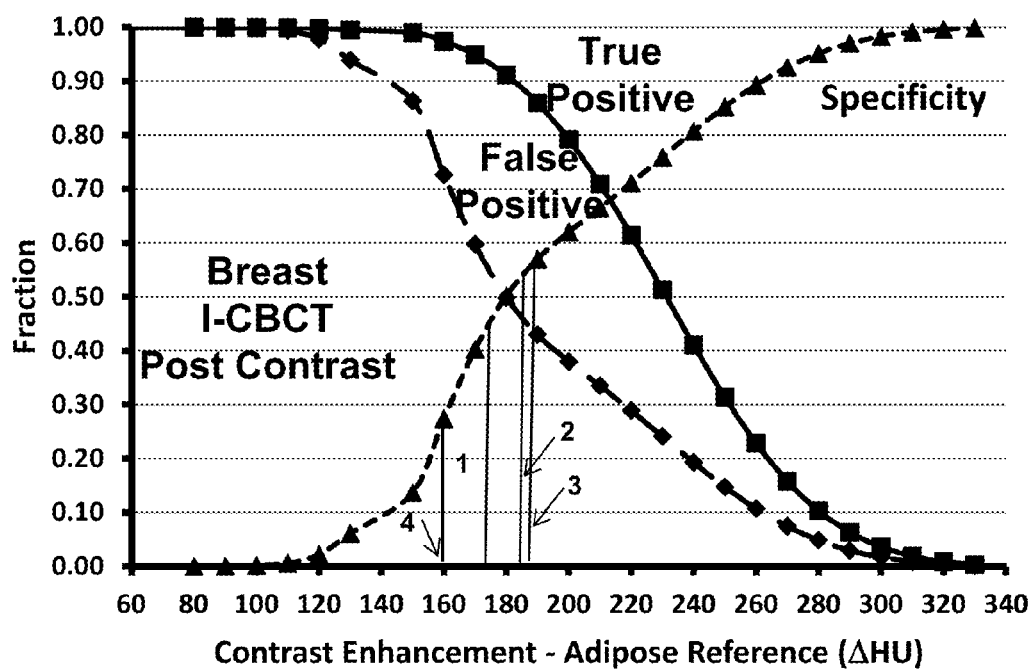
FIG. 17 illustrates an example quantitative metric constructed from the true positive fraction, false positive fraction, and specificity derived from the histogram data of FIG. 8 and being used to assess multiple nodules identified in a patient being evaluated.

In one embodiment, one set, as opposed to two sets, of CT data set with iodine contrast is acquired, eliminating the need for the "without iodine" data set and resulting in the reduction of the X-ray exposure dose by approximately half. Rather than relying on absolute HU values, which may be difficult to calibrate, the mean HU values of adipose tissue surrounding the nodule may be used as a reference to obtain ΔHU values. FIG. 17 illustrates an example quantitative metric constructed from the true positive fraction, false positive fraction, and specificity derived from the histogram data of FIG. 8, in accordance with one embodiment of the present disclosure. An example graph 1700 includes fractions as its vertical axis and ΔHU values as its horizontal axis.

Figure 18:
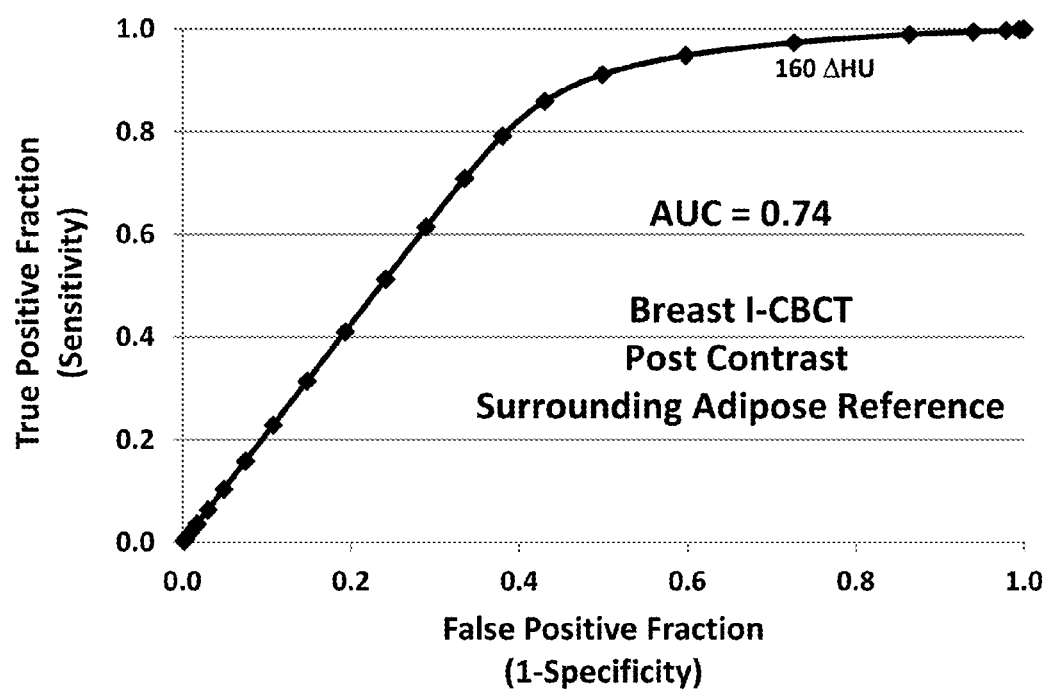
FIG. 18 illustrates an example quantitative metric from the histogram data similar to FIG. 8 and expressed in an annotated ROC curve.

FIG. 18 illustrates an example quantitative metric from the histogram data similar to FIG. 8 and expressed in an annotated ROC curve 1800, in accordance with one embodiment of the present disclosure. Variation of adipose tissue values and the inherent variability of the glandular tissues where breast cancer nodules occur contribute to a wider range of ΔHU values (than in FIG. 8). This additional uncertainty causes the AUC of the annotated ROC curve 1800 to be lower. Suppose the first four of the five nodules identified in the MIP image 1400 are plotted in the graph 1700 as shown in FIG. 17. The uncertainty drops the ranking of the nodule 4 below that of nodule 1 in disagreement with the ranking of the same four nodules shown in FIG. 15. This change in the ranking of the nodules is consistent with the degree of confidence lost when the AUC of the annotated ROC curve 1800 drops to a lower value than the AUC of the annotated ROC curve 1600.

To effectively manage cancer diseases, in addition to the standard anatomical criteria, functional information in the staging of lesions may be considered. For example, tumor growth rate (TGR) or equivalently tumor volume doubling time (TVDT) in solid lesions may be used to predict survival rate. FIG. 19(a) illustrates an example histogram of the frequency that a given TGR (described by a log doubling time) from analysis of X-ray screening mammogram lesions with a given growth rate in mammograms of breast cancer patients taken over time. By such as taking the logarithm of the TVDT, a distribution such as a normal bell shaped one shown in FIG. 19(a) is found, where the fastest growing portion is identified as Group A, and the second and the third portions are identified as Group B and Group C, respectively.

Figure 19:
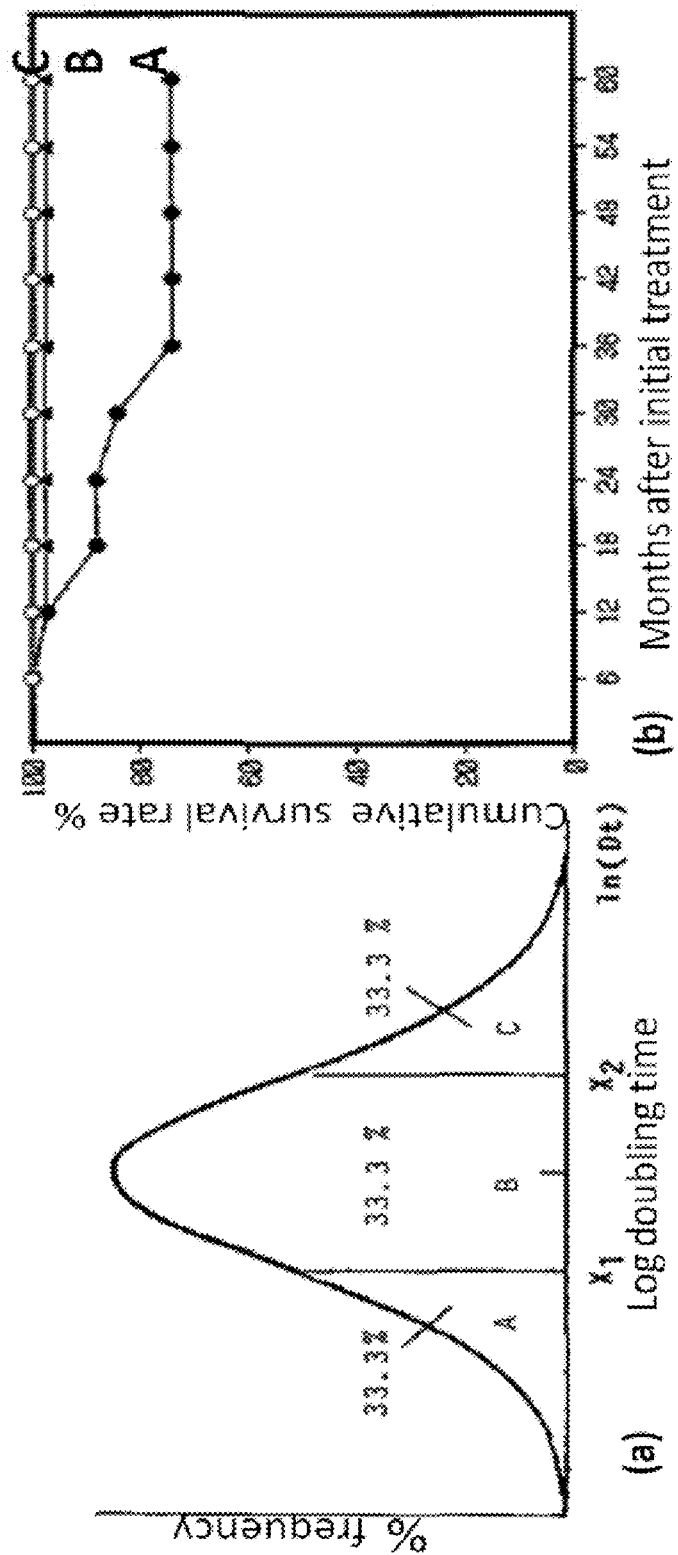
FIG. 19(*a*) illustrates an example histogram of the frequency that a given Tumor Growth Rate (described by a log doubling time) from analysis of X-ray screening mammogram lesions with a given growth rate in mammograms of breast cancer patients taken over time.

FIG. 19(b) illustrates a relationship between cumulative survival rates and months after initial treatment, in accordance with one embodiment of the present disclosure. In one implementation, after a 36-month follow up, Group A with the fast growth rates have the lowest survival percentage (less than 80%) compared to over 95% survival percentages for Groups B and C. The study related to FIG. 19 also includes measuring the microvessel densities of the biopsied lesions of the selected population of patients, and the study finds that the highest densities correlate with the fastest growth rates. However, in one embodiment, biomarkers such as iodine contrast enhancement are used, because their values should monotonically increase with MVDs. This is important because biomarker values can be obtained by in vivo imaging without the need for biopsy. Because of the leaky nature of microvessels, the higher their density the higher the contrast enhancement (e.g., the magnitude of the iodine concentration $I_c$ or the ΔHU value) may be expected.

Figure 20:
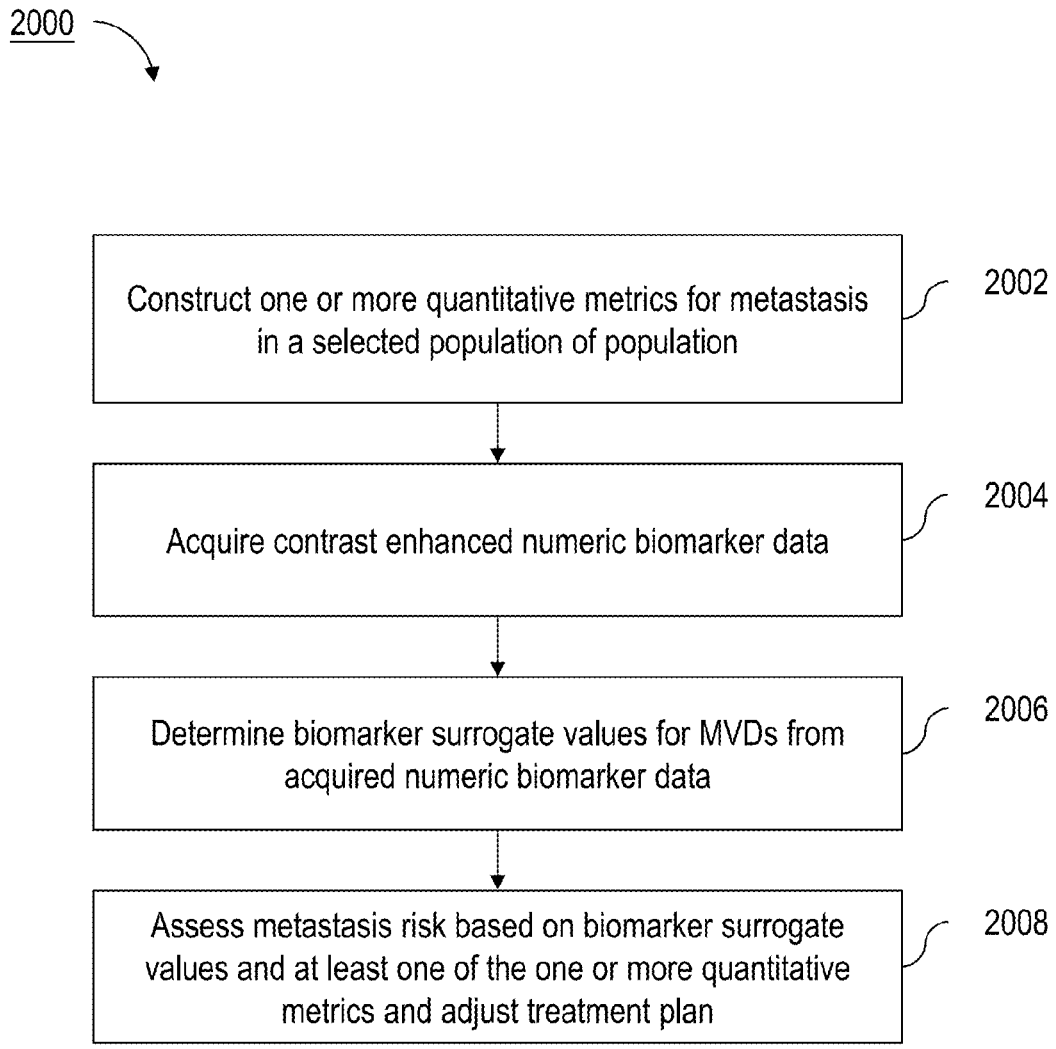
FIG. 20 illustrates an example method of identifying, assessing, and treating cancer growth rates and potential metastasis for a patient.

FIG. 20 illustrates an example method 2000 of identifying, assessing, and treating cancer growth rates and potential metastasis for a patient, in accordance with one embodiment of the present disclosure. The various blocks of the method 2000 are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. In one embodiment, biomarker values are measured with in vivo imaging without the need to perform biopsies to determine MVDs.

In block 2002 (prepare one or more quantitative metrics for metastasis in a selected population of patients), relevant data for a selected population of patients for metastasis is collected and analyzed, so that one or more quantitative metrics (for example, based on iodine contrast biomarker values) for the selected population of patients may be constructed. For tumors to grow, increased blood supply is essential resulting in generation of microvessels via angiogenesis. Thus, in one implementation, quantitative metrics as functions of microvessel densities (MVDs) correlated with metastasis occurrences are constructed. Alternatively, quantitative metrics may also be constructed as functions of biomarker values, instead of MVD values. Here, the biomarkers may also be referred to as biomarker surrogates of MVDs.

In block 2004 (acquire contrast enhanced numeric biomarker data), according to one embodiment of the present disclosure, a first set of numeric biomarker data associated with a patient being evaluated may be acquired before the injection of the biomarker into the patient (e.g., a contrast agent such as iodine), and a second set of numeric biomarker data may be acquired after the injection of the biomarker into the patient.

In block 2006 (determine biomarker surrogate values from acquired numeric biomarker data), the acquired numeric biomarker data is further processed to generate, for example, a mean HU value, a mean HU enhancement difference value, an increase in iodine contrast concentration $I_c$, and others. These enhancement contrast values may correspond to biomarker surrogate values for MVDs.

In block 2008 (assess metastasis risk based on biomarker surrogate values and at least one of the one or more quantitative metrics and adjust treatment plan), the biomarker surrogate values and their corresponding MDV information and the quantitative metrics may be utilized to help quantify metastasis risk. Since, as discussed above and in conjunction with FIG. 19, higher MDV corresponds to higher TGR, and higher TGR corresponds to higher fatality rate, treatment plan may be adjusted to more aggressively target the high growth nodules.

Figure 21:
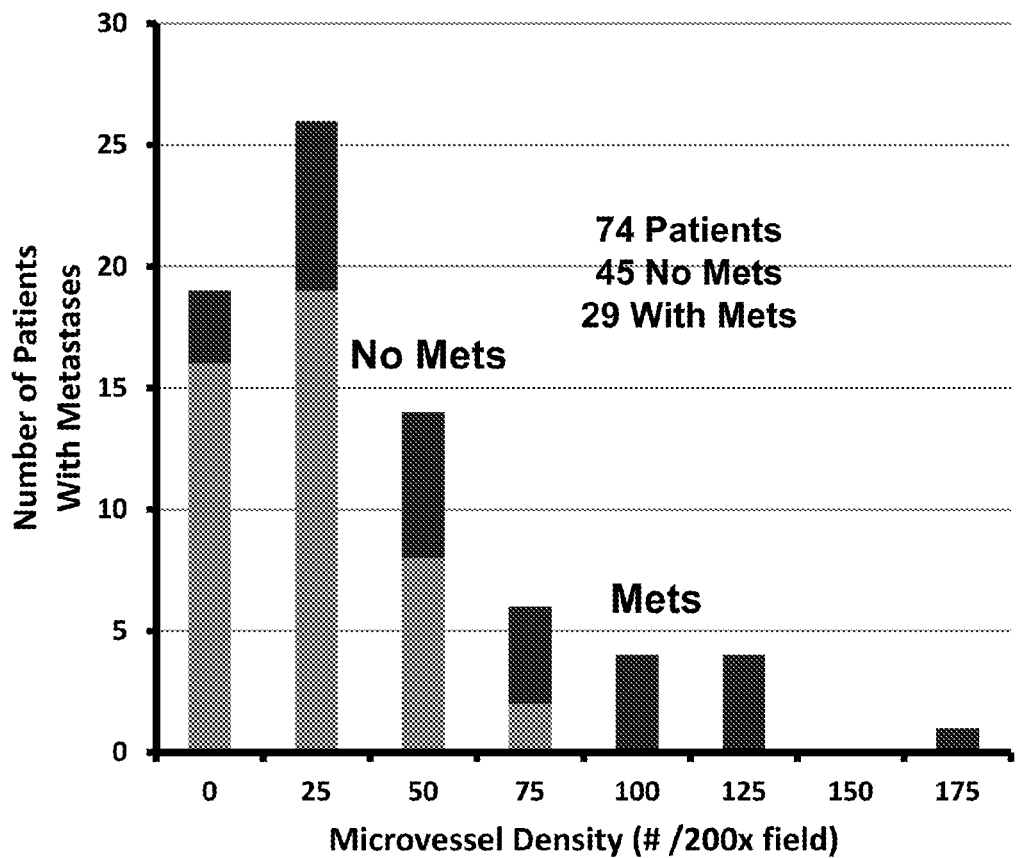
FIG. 21 illustrates an example histogram showing MVDs measured in prostates of a selected population of patients that are correlated with metastases occurrences.

FIG. 21 illustrates an example histogram 2100 showing MVDs measured in prostates of a selected population of patients that are correlated with metastases occurrences, in accordance with one embodiment of the present disclosure.

Figure 22:
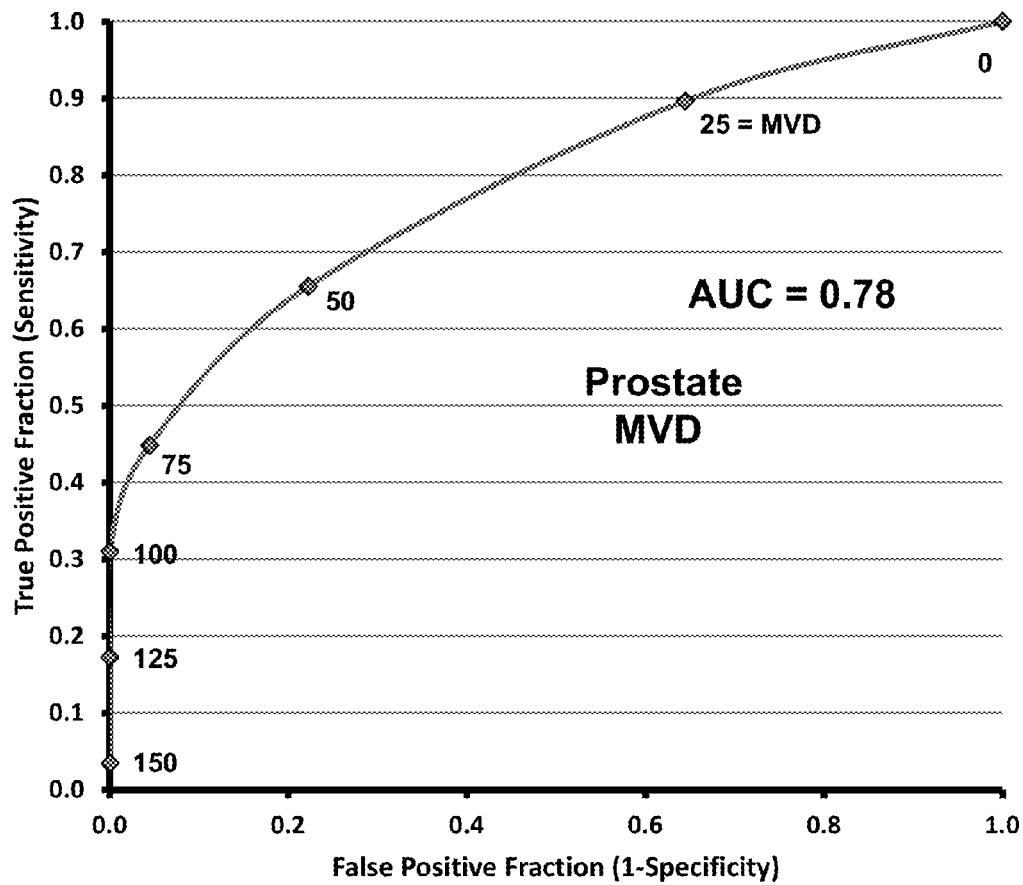
FIG. 22 illustrates an example quantitative metric constructed from the histogram data of FIG. 21 and expressed in an annotated ROC curve.

FIG. 22 illustrates an example quantitative metric constructed from the histogram data of FIG. 21 and expressed in an annotated ROC curve 2200, in accordance with one embodiment of the present disclosure. The vertical axis of the annotated ROC curve 2200 corresponds to TPFs, and the horizontal axis of the annotated ROC curve 2200 corresponds to FPFs. In addition, a threshold MVD value is placed adjacent to some of the data points plotted on the annotated ROC curve 2200. In one implementation, biomarker surrogate values, such as iodine concentration, versus MVDs in this selected population of patients are established, so that the MVD annotations of FIG. 22 also correspond to certain biomarker surrogate values. In another implementation, a similar curve as the annotated ROC curve 2200 may be constructed but with the biomarker surrogate values as its horizontal axis. Then, when the biomarker values (e.g., magnitude of $I_c$) of the patient being evaluated are obtained, such values can be assessed in view of either of the two aforementioned annotated ROC curves.

Figure 23:
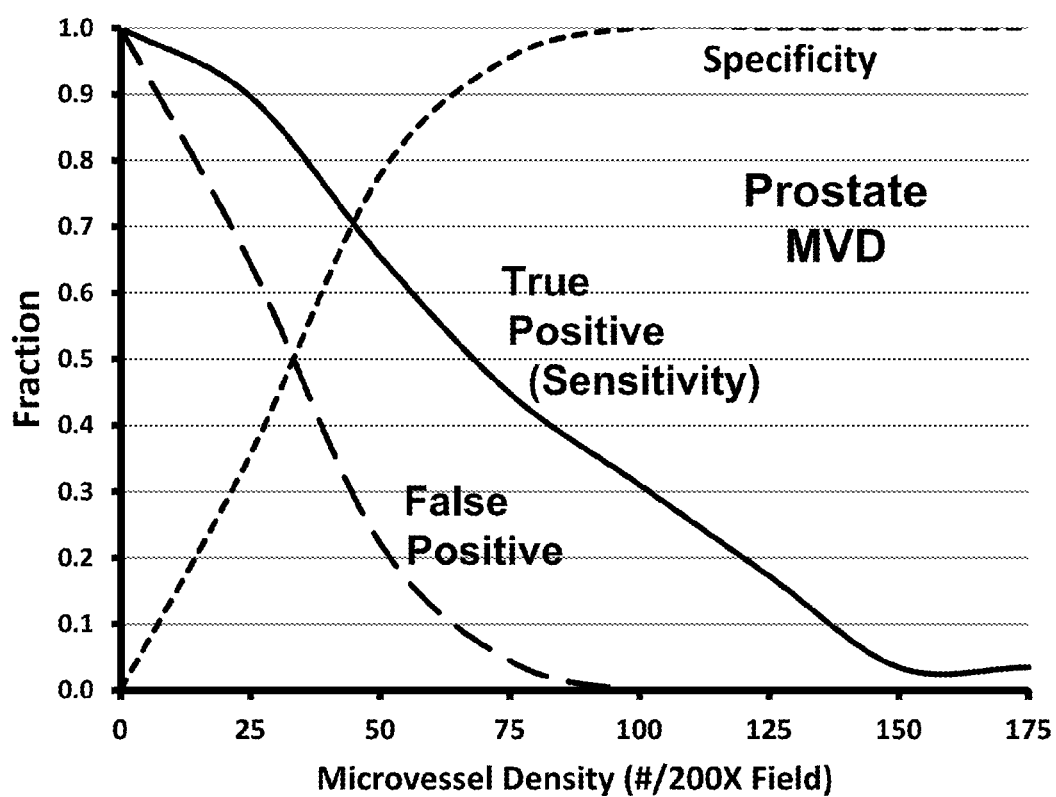
FIG. 23 illustrates an example quantitative metric constructed from the true positive faction, false positive fraction, and specificity derived from the histogram data of FIG. 21.

FIG. 23 illustrates an example quantitative metric constructed from the true positive faction, false positive fraction, and specificity derived from the histogram data of FIG. 21, in accordance with one embodiment of the present disclosure. An example graph 2300 includes fractions as its vertical axis and a set of MVDs as its horizontal axis. In another embodiment, biomarker values determined by in vivo imaging such as iodine contrast enhancement may be used as biomarker surrogate values for the MVDs, and a similar graph as the graph 2300 may be constructed using the biomarker values as its horizontal axis. With the use of such biomarker values, no actual biopsy is required. Similar to the discussions of FIG. 22. Then, when the biomarker values (e.g., magnitude of $I_c$) of the patient being evaluated are obtained, such values can be assessed in view of either of the two aforementioned graphs.

FIG. 24 is a block diagram illustrating a computer program product 2400 for identifying, assessing, and treating potential metastasis for a patient, in accordance with one embodiment of the present disclosure. The computer program product 2400 may include one or more sets of executable instructions 2402 for executing the methods described above and illustrated in FIG. 20. The computer program product 2400 may be transmitted in a signal bearing medium 2404 or another similar communication medium 2406. The computer program product 2400 may be recorded in a computer readable medium 2408 or another similar recordable medium 2410. In one embodiment, biomarker values are used as surrogates for the MVDs, so that biopsies are not required to accomplish the identification, assessment, and treatment operations.

Figure 25:
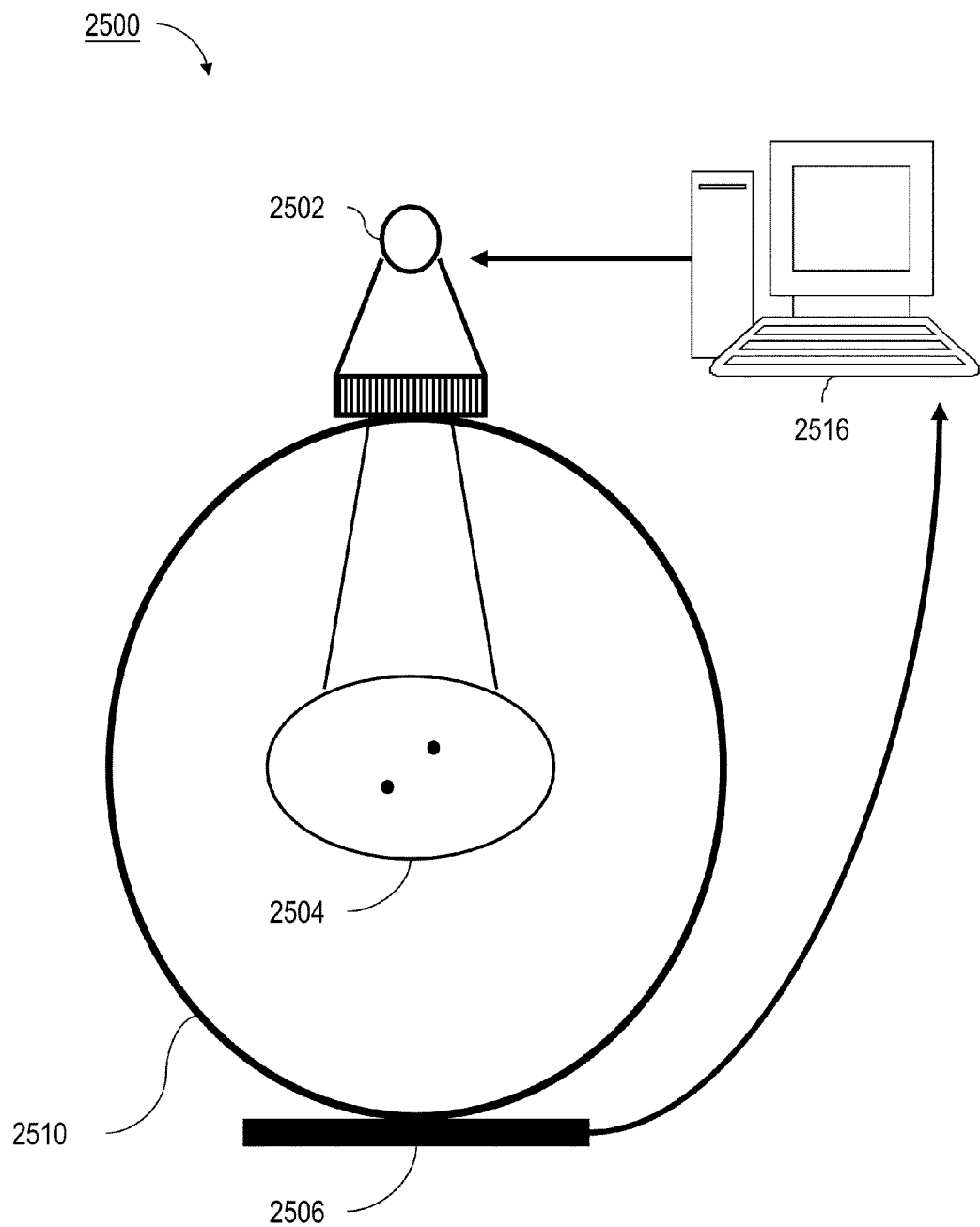
FIG. 25 is a schematic diagram illustrating a radiation system 2500, all arranged in accordance with some embodiments of the present disclosure.

FIG. 25 is a schematic diagram illustrating a radiation system 2500, in accordance with one embodiment of the present disclosure. The radiation system 2500 includes a radiation source 2502, an electronic portal imaging device (EPID) 2506, a gantry 2510, and a control system 2516. The radiation source 2502 is aimed towards a patient 2504 and to the EPID 2506.

In the illustrated embodiment, the control system 2516 includes a processor for executing instructions, such as the executable instructions 2402 shown in FIG. 24, a monitor for displaying data, and an input device, such as a keyboard or a mouse, for inputting data. Although the control system 2516 is shown as a separate component from the gantry 2510, in alternative embodiments, the control system 2516 can be a part of the gantry 2510.

It should be noted that the radiation system 2500 should not be limited to the configuration described above, and that the system can also have other configurations.

While the forgoing is directed to embodiments of the present disclosure, other and further embodiments of the present disclosure may be devised without departing from the basic scope thereof, and the scope thereof may be determined by the claims that follow.

We claim:

1. A method of identifying, assessing, and/or treating cancer growth for a patient, comprising:

constructing one or more improved quantitative metrics for metastasis in a selected population of other patients by developing a graphical representation based on a histogram that characterizes a relationship between occurrences of the metastasis and microvessel density information measured for the selected population of other patients, wherein the developed graphical representation includes either a Receiver Operator Characteristic (ROC) curve or at least one of a true positive fraction (TPF) curve, a false positive fraction (FPF) curve, and a Specificity curve, and one or more data points of the graphical representation is associated with at least one threshold microvessel value or at least one threshold biomarker surrogate value;

acquiring a first set of numeric biomarker data for the patient before having placed a biomarker in the patient;

acquiring a second set of numeric biomarker data for the patient after having placed the biomarker in the patient;

determining a set of mean numeric biomarker differences associated with one or more occurrences of the metastasis based on the first set of numeric biomarker data and the second set of numeric biomarker data, wherein the set of mean numeric biomarker differences correspond to biomarker surrogate values for microvessel density information;

predicting quantitative and objective risk for the patient's metastasis based on the biomarker surrogate values and at least one of the one or more improved quantitative metrics for the metastasis in the selected population of other patients, developing a treatment plan for the cancer growth of the patient based on the predicted quantitative and objective risk for the patient's metastasis; and administering the treatment plan to the patient to target the specific nodules of the patient.

2. The method of claim 1, wherein the first set of numeric biomarker data and the second set of numeric biomarker data are obtained by in vivo imaging.

3. The method of claim 1, wherein values of the biomarker monotonically increase with the microvessel density information.

4. The method of claim 1, wherein the one or more improved quantitative metrics characterize a relationship between tumor growth rate and survival rate of the selected population of other patients.

5. The method of claim 4, further comprising:

identifying nodules of the patient that are associated with the metastasis having high tumor growth rate; and adjusting the treatment plan for the patient by treating the identified nodules at a higher priority than other nodules of the patient.

6. The method of claim 1, wherein the constructing one or more improved quantitative metrics further comprises:
associating the at least one threshold microvessel value or the at least one threshold biomarker surrogate value with one or more of the data points of the ROC curve, wherein each of data points of the ROC curve corresponds to a TPF and a FPF.

7. The method of claim 1, wherein the developed graphical representation has a vertical axis corresponding to fractions and a horizontal axis corresponding to a set of microvessel density information or a set of biomarker surrogate values.

8. The method of claim 1, wherein the set of mean numeric biomarker differences correspond to a set of mean Hounsfield Unit (HU) enhancement differences or a set of increases in iodine contrast concentration.

\* \* \* \* \*

UNITED STATES PATENT AND TRADEMARK OFFICE
CERTIFICATE OF CORRECTION

| | | |
|---|---|---|
| PATENT NO. | : 8,935,099 B2 | Page 1 of 1 |
| APPLICATION NO. | : 13/623098 | |
| DATED | : January 13, 2015 | |
| INVENTOR(S) | : Larry Partain et al. | |

It is certified that error appears in the above-identified patent and that said Letters Patent is hereby corrected as shown below:

In the Claims

In Column 10, Lines 39 - 40, Claim 1, please delete "the metastasis" and insert -- the patient's metastasis --, therefor.

In Column 10, Line 49, Claim 1, please delete "other patients," and insert -- other patients; --, therefor.

Signed and Sealed this
Fourteenth Day of July, 2015

Michelle K. Lee
*Director of the United States Patent and Trademark Office*